US011998724B2

(12) United States Patent
Klemm et al.

(10) Patent No.: US 11,998,724 B2
(45) Date of Patent: Jun. 4, 2024

(54) INJECTION DEVICE

(71) Applicant: Sanofi-Aventis Deutschland GMBH, Frankfurt am Main (DE)

(72) Inventors: Thomas Klemm, Frankfurt am Main (DE); Stephan Mueller-Pathle, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 15 days.

(21) Appl. No.: 17/727,423

(22) Filed: Apr. 22, 2022

(65) Prior Publication Data
US 2022/0241511 A1     Aug. 4, 2022

Related U.S. Application Data

(63) Continuation of application No. 16/467,305, filed as application No. PCT/EP2017/081775 on Dec. 7, 2017, now Pat. No. 11,338,094.

(30) Foreign Application Priority Data

Dec. 8, 2016   (EP) ..................................... 16202980

(51) Int. Cl.
*A61M 5/315*   (2006.01)
*A61M 5/24*    (2006.01)
*A61M 5/32*    (2006.01)

(52) U.S. Cl.
CPC .......... *A61M 5/31553* (2013.01); *A61M 5/24* (2013.01); *A61M 5/3202* (2013.01); *A61M 2205/50* (2013.01)

(58) Field of Classification Search
CPC .. A61M 5/31553; A61M 5/24; A61M 5/3202; A61M 2205/50
See application file for complete search history.

(56) References Cited

U.S. PATENT DOCUMENTS 11,338,094 B2 *  5/2022  Klemm ............. A61M 5/31553
2004/0207385 A1  10/2004  Gafner et al.
(Continued)

FOREIGN PATENT DOCUMENTS

CA    2776870       4/2011
CN    102170929 A   8/2011
(Continued)

OTHER PUBLICATIONS

International Preliminary Report on Patentability in International Appln. No. PCT/EP2017/081775, dated Jun. 11, 2019, 7 pages.
(Continued)

*Primary Examiner* — Tasnim Mehjabin Ahmed
(74) *Attorney, Agent, or Firm* — Fish & Richardson P.C.

(57) ABSTRACT

An injection device for administering a dose of a liquid medicament includes an elongated housing having a dispensing end and being configured to accommodate a cartridge filled with the liquid medicament, a drive mechanism configured to operably engage with the cartridge for expelling of a dose of the medicament from the cartridge via the dispensing end, a protective cap releasably attachable to the housing to cover the dispensing end, a first electronic circuit attached to the protective cap and electrically connected to at least a first cap electrode arranged on the protective cap, and a second electronic circuit arranged inside the housing, coupled to the drive mechanism and electrically connected to at least a first housing electrode that is located on the housing.

19 Claims, 3 Drawing Sheets

(56) References Cited

U.S. PATENT DOCUMENTS

| | | | | |
|---|---|---|---|---|
| 2011/0190705 A1* | 8/2011 | Mernoe | ............ | A61M 5/14566 604/152 |
| 2011/0295215 A1* | 12/2011 | Nielsen | ................. | G16H 20/17 604/257 |
| 2014/0107585 A1 | 4/2014 | Eggert et al. | | |
| 2015/0224259 A1 | 8/2015 | Giambattista et al. | | |
| 2016/0213853 A1 | 7/2016 | Despa et al. | | |
| 2017/0224922 A1 | 8/2017 | Lepple-Wienhues | | |

FOREIGN PATENT DOCUMENTS

| | | |
|---|---|---|
| CN | 103648561 | 3/2014 |
| CN | 104379195 A | 2/2015 |
| CN | 105102032 | 11/2015 |
| CN | 105102043 A | 11/2015 |
| JP | H04-312469 A | 11/1992 |
| JP | 2009-050709 | 3/2009 |
| JP | 2012-504440 | 2/2012 |
| JP | 2013-507159 | 3/2013 |
| JP | 2014-514120 A | 6/2014 |
| JP | 2014-519901 | 8/2014 |
| JP | 2014-520616 A | 8/2014 |
| JP | 2014-525326 A | 9/2014 |
| JP | 2016-512966 | 5/2016 |
| JP | 2016-518903 | 6/2016 |
| JP | 2016-520358 A | 7/2016 |
| WO | WO 2003/009461 | 1/2003 |
| WO | WO 2010/037828 | 4/2010 |
| WO | WO 2011/042540 | 4/2011 |
| WO | WO 2012/152628 A1 | 11/2012 |
| WO | WO 2012/160163 | 11/2012 |
| WO | WO 2013/010889 A1 | 1/2013 |
| WO | WO 2013/033467 A2 | 3/2013 |
| WO | WO 2013/120775 | 8/2013 |
| WO | WO 2014/111341 | 7/2014 |
| WO | WO 2014/166908 | 10/2014 |
| WO | WO 2014/166926 | 10/2014 |
| WO | WO 2014/173772 A1 | 10/2014 |
| WO | WO 2016/020276 | 2/2016 |

OTHER PUBLICATIONS

International Search Report and Written Opinion in International Appln. No. PCT/EP2017/081775, dated Feb. 12, 2018, 9 pages.

* cited by examiner

INJECTION DEVICE

CROSS REFERENCE TO RELATED APPLICATIONS

The present application is a continuation of U.S. patent application Ser. No. 16/467,305, filed on Jun. 6, 2019, which is the national stage entry of International Patent Application No. PCT/EP2017/081775, filed on Dec. 7, 2017, and claims priority to Application No. EP 16202980.5, filed on Dec. 8, 2016, the disclosures of which are incorporated herein by reference.

TECHNICAL FIELD

The present disclosure relates to the field of injection devices and in particular to manually operated injection devices, such as and held pen-type injectors. In one aspect an electronic measurement of a dose of a medicament actually set or dispensed by the injection device is provided.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices such like pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction, i.e. in a dispensing direction and may therefore expel a predefined amount of the medicament via a piercing assembly, which is to be releasably coupled with a distal end section of the housing of the drug delivery device.

The medicament to be dispensed by the drug delivery device is typically provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

When using such pen-type injection devices rather frequently it is desirable to provide an automated logging or capturing of dispensing-related data. It is generally desirable to record and to monitor the time and the date of medicament dispensing or medicament injection as well as the amount of medicament that has been dispensed or injected. There exist injection devices that are driven by an electromechanical drive in connection with an electronic control logic. Such devices are rather expensive and susceptible to damage. There exist other solutions such as described in WO 2013/120775 A1. There, an electronic clip-on module is described for a manually operable pen-type injection device. The electronic clip-on module has a body and a mating unit configured to releasably mount the module to the injection device in a specific position relative to an outside surface thereof.

Such electronic clip-on modules are capable to monitor and to log dose sizes as well as date and time of a dispensing procedure. The correct use of such clip-on modules requires a well-defined attachment to the injection device, which sets certain demands for an end user especially in view of his handling skills. This problem further exacerbates for users or patients suffering an impaired vision or that suffer from tremor of the hands. Apart from that the clip-on module modifies the outer appearance of the handheld and portable injection device. End users may therefore be rather reluctant or may hesitate to keep the add-on module permanently attached to the injection device, especially when carrying the injection device along.

Among pen-type injection devices there exist so-called reusable devices that provide a reset function of a drive mechanism and which are further configured for replacement of an empty cartridge. Contrary to this, so-called disposable or prefilled injection devices are void of a reset function of their drive mechanism and are intended and configured to be discarded entirely after the content of the cartridge, e.g. the medicament, has been used up. Such disposable injection devices are rather easy to handle and can be operated by end users and patients already with a minimum of handling skills or training. Since there is no need for cartridge replacement and since the devices are intended to be used only for a limited time period they can be manufactured in large quantities at moderate costs. Typically, disposable injection devices are implemented as all mechanical injection devices. Just for cost-saving reasons they are typically void of electronic components or of an electromechanical drive inside a housing.

SUMMARY

In certain aspects, an improved manually or mechanically operated handheld injection device for administering a dose of a liquid medicament providing a logging and monitoring of dispensing-related data is provided. The injection device and the data logging or dispensing monitoring can be highly attractive for end consumers or patients. The data logging or dispensing monitoring function can be implemented in the injection device without any further interference with the end user or patient. It can be highly reliable and should be highly acceptable by end users or patients. Manufacturing of the injection device can be rather cost efficient. In addition, the geometric size and/or the outer appearance of the injection device can be unaffected by the implementation of a data logging or dispensing monitoring function.

In one aspect an injection device for administering a dose of a liquid medicament is provided. The injection device comprises an elongated housing having a dispensing end and being configured to accommodate a cartridge filled with the liquid medicament. The elongated housing is of substantially cylindrical or oval shape. The injection device may be configured as a pen-type injector. It comprises a drive mechanism located inside the housing and being configured to operably engage with the cartridge for expelling of a dose of the medicament from the cartridge via the dispensing end. The dispensing end is typically releasably connectable with a needle assembly having a double-tipped injection needle. When attached to the dispensing end the injection needle is in fluid communication with the interior of the cartridge. The drive mechanism typically comprises at least a piston rod that is configured to be driven and to be displaced in an axial direction, i.e. substantially parallel to the elongation of the housing or parallel with the long axis of the tubular-shaped cartridge.

The injection device further comprises a protective cap releasably attachable to the housing to cover and/or to enclose the dispensing end. The protective cap is detachably connectable to the housing, either to the dispensing end or to a proximal portion of the housing, e.g. a body portion of the housing that substantially houses and accommodates the drive mechanism. The protective cap may be of substantially cylindrical shape with a closed distal end and with an opening towards its proximal end. When attached to the housing the dispensing end of the injection device is received and accommodated inside the protective cap.

The injection device further comprises a first electronic circuit that is attached to the protective cap. There is further provided a first cap electrode on the protective cap. The first cap electrode is electrically connected to the first electronic circuit. There is provided a second electronic circuit arranged inside the housing of the injection device. The second electronic circuit is coupled or connected to the drive mechanism. The second electronic circuit is also electrically connected to at least a first housing electrode that is located on the housing of the injection device. First and second electronic circuits are electrically connected to each other via the at least first cap electrode and the at least first housing electrode. The protective cap, the position of the first cap electrode, the geometric shape of the housing, in particular of its dispensing end and the position and location of the at least first housing electrode is selected and configured such, that the at least first housing electrode and the at least first cap electrode are in electric contact when the protective cap is attached to the dispensing end of the housing.

Typically, the housing and the protective cap comprise mutually engaging fastening elements, such like positively engaging protrusions or recesses by way of which the protective cap can be attached and secured to the housing in a well-defined manner.

By providing a first electronic circuit to or in the protective cap and by providing a second electronic circuit inside the housing of the injection device a kind of a hybrid injection device is provided. It is particularly the first electronic circuit that acts and behaves as a kind of a main electronic circuit whereas the second electronic circuit is configured as an auxiliary electronic circuit. While the second electronic circuit comprises a rather limited functionality the first electronic circuit may provide the main functionalities and hardware as well as software components that are necessary to implement a data logging and/or dispensing monitoring.

In this way the second electronic circuit is a kind of a cut-down electronic circuit that is void of a transceiver and void of an own energy supply. The second electronic circuit is particularly configured and designed as a disposable electronic circuit that can be discarded with the housing of the injection device after the content of a cartridge has been used up. Contrary to that the first electronic circuit is a rather sophisticated multifunctional electronic circuit. Consequently, the cap provided with the first electronic circuit is configured and designed as a reusable cap that can be reused with a series of housings that are equipped with a cartridge and a drive mechanism. In this way the protective cap with the first electronic circuit comprises the most expensive and sophisticated electronic components that are required for the implementation of a data logging or dispensing monitoring.

Since the protective cap and its first electronic circuit is intended for reuse, i.e. for use with multiple housings and multiple second electronic circuits the protective cap must be purchased only once, e.g. in a starter kit including the housing and the protective cap. Once the content of a cartridge has been used up the housing is to be replaced by a new one while keeping the protective cap. In this way a rather elegant, cost-efficient and space-saving solution for data logging and dispensing monitoring with disposable devices is provided. Moreover, when using the cap with different housings data logging and dispensing monitoring can be performed simultaneously with numerous injection devices.

Since the first electronic circuit is typically located inside the cap and since the second electronic circuit is arranged inside the housing the electronic circuits are not visible from outside. Implementation of a data logging or dispensing monitoring function in an existing injection device geometry can be rather smooth. The implementation is hardly visible from outside. Implementation of the data logging and/or dispensing monitoring has no negative impact on the outer appearance of the injection device or on the user acceptance of such injection devices.

According to another embodiment the first electronic circuit comprises a first battery, an electric power supply and a first logic circuit to process electric signals received from the second electronic circuit. In some embodiments the second electronic circuit and hence the entire housing may be void of an own battery or of an own energy supply. An energy supply for the second electronic circuit may be exclusively provided by the first battery of the first electronic circuit. However, there are other embodiments, wherein also the second electronic circuit comprises at least a small battery that may be rechargeable.

With the first electronic circuit comprising a first battery and a first logic circuit it is generally possible that the second electronic circuit is void of a logic circuit as well as void of an own battery. In this way, manufacturing costs for the second electronic circuit can be kept at a minimum, thereby enabling to keep the costs for the disposable housing of the injection device at a moderate or minimum level.

According to another embodiment also the second electronic circuit comprises a second logic circuit to capture dose dispensing-related data from the drive mechanism and to transmit captured data to the first logic circuit via the at least first cap electrode and the at least first housing electrode. The second logic circuit may be a cut-down version of the first electronic circuit. Its functionality may be rather limited compared to the functionality of the first electronic circuit.

It is particularly intended, that only the first electronic circuit is provided with a transceiver, either a wireless or wired transceiver to transmit captured data or monitored dispensing information to an analysis tool such as a personal computer, a tablet computer, a smartphone or the like that provides comprehensive data analysis.

In another embodiment it is generally conceivable, that there are provided several cap electrodes on the protective cap and that there are provided also several housing electrodes on the housing. For instance there may be provided two or three cap electrodes each of which configured to get in electric contact with one of the housing electrodes when the protective cap is correctly assembled to the housing. Some of the cap electrodes and housing electrodes may provide an energy supply for the second electronic circuit and/or for the second logic circuit whereas other cap electrodes or housing electrodes may provide data transmission between the first and second electronic circuit, hence between the first and the second logic circuits thereof. It is also conceivable, that there are provided two cap electrodes in contact with two housing electrodes, wherein the cap electrodes and the housing electrodes provide both, power supply for the second electronic circuit and optionally for the second logic circuit as well as data transmission or signal transmission between the first electronic circuit and the second electronic circuit.

In another embodiment the second logic circuit is powered by the first battery when the protective cap is attached to the housing. With this embodiment there are typically provided a first and a second cap electrode in contact with a first and with a second housing electrode. The cap electrodes are in electric contact with the first battery and hence with the first electronic circuit whereas the first and the second housing electrodes are in electric contact with the second electronic circuit and hence with the second logic circuit. In some embodiments it is conceivable, that the second logic circuit is exclusively powered by the first battery of the first electronic circuit, i.e. when the protective cap is correctly assembled to the housing. Attaching the protective cap to the housing may wake up the second logic circuit or may further introduce a predefined function of the logic circuit, such as transmitting of previously captured signals or data that may be stored in a non-volatile memory, such like a flash-type memory.

In a further embodiment the second electronic circuit comprises a re-chargeable second battery. The second battery is chargeable or re-chargeable by the first battery when the protective cap is attached to the housing. The second battery may be configured and designed as a battery with a rather limited capacity. The capacity of the second battery may be just as large as to monitor or to capture a single or a few dose dispensing procedures. The second battery may comprise a condensator or a set of electronic charge accumulating condensators. Moreover, it is conceivable, that the re-chargeable second battery comprises a capacity that is sufficient to power the second logic circuit over a comparatively limited time interval, such like 10 minutes, 20 minutes, 30 minutes, 1 hour or more. Typically, the capacity of the second battery is dimensioned such that the second electronic circuit is operable for a limited time, less than 90 minutes, less than 60 minutes or less than 30 minutes.

Once the protective cap is detached from the housing the second and re-chargeable battery may provide a standalone operation of the second electronic circuit in order to monitor and to capture dose dispensing-related signals, data and information. Upon reattachment of the cap to the housing an electric contact between the second electronic circuit and the first battery is re-established and data, information or signals previously logged and captured by the second electronic circuit can be transmitted by wire to the first electronic circuit.

The re-charging of the second battery comes along with a series of advantages. First of all, the geometric dimensions of the second battery can be kept rather small, the total costs for manufacturing and for implementing such tiny second batteries can be kept at a low or moderate level. Moreover, an inevitable environmental burden upon discarding of the housing with the second electronic circuit arranged therein can be kept at a minimum level. At the same time the re-chargeable second battery provides at least a limited time of standalone operation of the second logic circuit and the second electronic circuit even with the protective cap detached and separated from the housing.

In another embodiment the drive mechanism of the injection device comprises at least one of:
  a) a dose selector to set a dose of the medicament of variable size, wherein the dose selector is audibly moveable relative to the housing at predefined discrete steps, and
  b) a dose button audibly moveable relative to the housing to trigger or to control a medicament dispensing procedure.

Selecting of a dose may be conducted by a dose selector that is e.g. rotatably supported at or near a proximal end of the housing of the injection device. Dose setting or dialing of a dose may be accompanied by a click sound audibly and/or haptically indicating to a user, that the actually set dose is incremented or decremented by a discrete step. The dose button, typically arranged at the distal end of the housing, hence opposite to the dispensing end is typically depressible in distal direction, e.g. by a thumb of a user, in order to trigger and/or to control a dispensing procedure. Typically, premature release of the dose button may immediately interrupt an ongoing dispensing procedure.

The displacement of a dose button relative to the housing for the purpose of dispensing or interrupting of a dose setting procedure may also be accompanied by a characteristic noise or sound. The noise or sound producible with a movement of the dose button may clearly distinguish from the noise or click sound generated by a movement, e.g. a dialing operation of the dose selector. In this way, one may acoustically distinguish between a dose setting procedure and a dose dispensing procedure.

Most available handheld and manually operated injection devices provide respective and rather characteristic click noises during dose setting as well as during dose dispensing. An acoustic or haptic pulse may be easily recorded and captured by at least one of the first and second electronic circuits or by at least one of the first and second logic circuits thereof.

In another embodiment the first electronic circuit comprises a microphone or a noise detector to detect successive dose incrementing steps or dose decrementing steps of a dose selector's movement and/or to detect an audible movement of the dose button. Implementation of a microphone in the first electronic circuit comes along with the integration of a microphone into the protective cap. Since the protective cap is intended for reuse the rest of the injection device, hence the housing, the drive mechanism and all components located inside the drive mechanism can be kept void of a microphone. Including a microphone in the first electronic circuit is therefore a rather cost alternative solution for capturing and monitoring a dose dialing and/or dose dispensing procedure acoustically.

The first electronic circuit is typically provided with a counter to count successive click noises recorded and captured by the microphone. In this way a size of a dose can be acoustically determined.

It is particularly conceivable, that an acoustic surveillance is triggered via the wired connection between the first and the second electronic circuits. In another embodiment the second electronic circuit comprises at least one contact switch connected to the at least one housing electrode and connected to the drive mechanism. The at least one contact switch of the second electronic circuit may be further in contact with the second logic circuit. Depending on the specific implementation dialing of a dose or dispensing of a dose may be directly detected by the contact switch. Hence, the contact switch may be mechanically connected to at least one of the dose selector and the dose button. Dialing of the dose selector and/or depressing of the dose button may close the contact switch, thereby powering up at least one of the first and second logic circuits for the purpose of data logging or dispensing monitoring.

In typical embodiments there are provided at least two contact switches by way of which the second electronic circuit and/or the second logic circuit may distinguish between a dose incrementing or dose decrementing actuation or a respective movement of the dose selector.

With at least one or with first and second contact switches of the second electronic circuit the second electronic circuit can be configured without a second logic circuit. In a rather simple and cost-efficient embodiment it is generally conceivable, that the second electronic circuit essentially consists of the two contact switches and a first and a second housing electrode. In this case, electric signals generated by the contact switches during dose selecting can be transferred wire-based and via housing electrodes and cap electrodes to the first electronic circuit and the first logic circuit. The entire signal and data processing for the data logging or dispensing monitoring function may then be conducted and performed exclusively by the first electronic circuit and its first logic circuit. In such embodiments the second electronic circuit can be void of a second logic circuit and void of an own second battery.

In another embodiment the drive mechanism of the injection device comprises a number sleeve or dose size indicating sleeve that is rotatably supported inside the housing. The number sleeve comprises a pattern of dose size indicating numbers on an outside surface thereof. The number sleeve further comprises an electric resistor strip extending on the outside surface of the number sleeve in accordance with the pattern. The electric resistor strip may be axially offset to the dose size indicating numbers. The electric resistor strip may alternatively overlap with the dose size indicating numbers. The electric resistor strip may comprise a transparent electrically resistive material in order to avoid obscuring of the dose size indicating numbers. The pattern of dose size indicating numbers may be also axially offset in its entirety from the electric resistor strip. But then the overall shape and geometry of the pattern and the electric resistor strip may be highly similar or even identical.

With an electric resistor strip a degree of rotation of the number sleeve, e.g. during a dose setting procedure and/or during a dose dispensing or dose injection procedure can be precisely monitored and measured. An electric resistor strip is rather easy and cost-efficient to implement onto a number sleeve. For instance, the electric resistor strip may be simply printed on the outside surface of the housing.

By means of an electric resistor strip a rotation of the number sleeve in either direction can be detected and quantitatively measured. In addition to a quantitative or absolute measurement of a degree of rotation, consecutive rotations in opposite directions could be easily compared with each other. It can be measured if the degree of rotation in one direction equals the degree of rotation in the opposite direction. This can be done by determining the electrical resistance at the beginning of a rotation in one direction and comparing the determined electrical resistance with a corresponding electrical resistance at the end of rotation in the opposite direction. Alternatively, the difference of the electrical resistance at the beginning and at the end of rotation in one direction can be compared to the difference of the electrical resistance at the beginning and at the end of rotation in the opposite direction.

Measuring the degree of rotation during dose setting could be used to determine a size of a dose currently set. Measuring the degree of rotation during dose dispense could in this way be used to determine the dose that is actually expelled or ejected. Measuring the degree of rotation in both directions, i.e. during dose setting and during dose dispensing could in this way be used to check if the set dose is actually completely and correctly dispensed or ejected.

In another embodiment the second electronic circuit comprises at least a first contact electrode in contact with the electric resistor strip. The first contact electrode is moveable relative to the number sleeve. If the number sleeve is axially fixed inside the housing and is rotatable with regard to the housing it is sufficient when the first contact electrode is slidably supported in the housing along the housing's longitudinal direction. In this way, the first contact electrode may follow the electric resistor strip during setting or dialing of a dose. It is intended, that the first contact electrode is permanently in electrical contact with the electric resistor strip so as to enable a permanent electric resistivity measurement of the resistor strip being indicative of a size of a dose actually set.

In another embodiment the electric resistor strip helically winds around the outside surface of the number sleeve. In addition to that one longitudinal end of the resistor strip is electrically connected with a first annular tab. Another longitudinal end of the resistor strip is connected with a second annular tab. First and second annular tabs are also located on the outside surface of the number sleeve. As seen in axial or longitudinal direction of the number sleeve the electric resistor strip is axially sandwiched between the first annular tab and the second annular tab.

By means of first and second annular tabs a total electric resistivity of the electric resistor strip can be measured. The electric resistivity of the resistor strip may be subject to environmental influences, such as ambient temperature. In order to keep the production and manufacturing costs at a moderate level it is of particular benefit when the technological demands to the electric resistor strip are kept on a rather low level.

The first and second annular tabs electrically connected with opposite ends of the electric resistor strip enable and provide measurement of the total electric resistivity of the resistor strip. By means of the first contact electrode, the electric resistivity of a portion or section of the electric resistor strip can be measured.

Making use of first and second annular tabs in combination with the first contact electrode enables a rather precise and temperature independent resistivity measurement of the electric resistor strip on the basis of which the degree of rotation of the number sleeve and hence a size of a dose actually set can be determined.

In another embodiment the second electronic circuit further comprises a second contact electrode in contact with the first annular tab. The second electronic circuit further comprises a third contact electrode in contact with the second annular tab. By having altogether a first, a second and a third contact electrode at least two different resistivity measurements of the electric resistor strip can be performed, thereby compensating any measurement defects that may be due to a varying environmental influences, such as a varying temperature.

In a further embodiment the first contact electrode is attached to a gauge element having a gauge window and covering at least a portion of the number sleeve. The gauge element is threadedly engaged with the number sleeve and it is further rotationally locked to the housing. Typically, the gauge element is splined to the housing, e.g. by means of at least one radial protrusion engaged in a radial recess supporting and allowing a sliding motion of the gauge element along the housing's longitudinal elongation. With the number sleeve axially constrained or axially fixed inside the housing and with the threaded engagement with the gauge element it is actually the gauge element that is subject to a longitudinal or axial sliding motion as the number sleeve is subject to a rotation.

The gauge window, typically in form of an aperture in the gauge element slides in axial direction over the outside surface of the number sleeve and the pattern of dose size indicating numbers. With a helical pattern of dose size indicating numbers having a lead that corresponds to the lead of the threaded engagement of the gauge element, successively increasing or decreasing numbers of the helical pattern will show up in the gauge window as a dose is incremented or decremented during a dose setting procedure or during a subsequent dose dispensing procedure during which the number sleeve is subject to a respective rotation. With the first contact electrode attached to the gauge element the first contact electrode may remain in permanent electrical contact with the electrical resistor strip. The electric resistivity measured between the first contact electrode and one of the second or third contact electrodes is therefore directly indicative of the size of a dose actually set.

According to another embodiment at least one of the first logic circuit and the second logic circuit is configured to calculate a ratio of a first electrical resistivity and a total electric resistivity. The first electrical resistivity is measurable between the first contact electrode and one of the second or third contact electrodes. The total electrical resistivity is measurable between the second contact electrode and the third contact electrode, hence through contact with first and second annular tabs at opposite longitudinal ends of the helically-shaped electrical resistor strip. Dividing of the first electrical resistivity by the total electrical resistivity is beneficial in order to compensate any offset effects that may arise due to varying ambient temperatures. The ratio of the first electrical resistivity divided by the total electrical resistivity is identical to the ratio of the dose size actually set divided by the maximum dose size injectable by the injection device.

In another embodiment the injection device is further provided with a cartridge arranged inside the housing and being filled with a liquid medicament. The injection device is particularly of pre-filled type. Hence, a cartridge filled with the medicament is readily assembled inside the housing of the injection device.

Typically, the electric resistor strip comprises a rather homogeneous and linear resistivity along its elongation. So the resistivity of a section of the electric resistor strip is always proportional to the elongation or geometric extension of the said portion. Typically, the total resistivity of the electric resistor strip is directly proportional to the length of the electrical resistor strip.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as defined by the appending claims. Further, it is to be noted, that any reference numerals used in the appended claims are not to be construed as limiting the scope of the invention.

BRIEF DESCRIPTION OF THE FIGURES

In the following, embodiments are described in detail by making reference to the drawings, in which.

DETAILED DESCRIPTION

Figure 1:
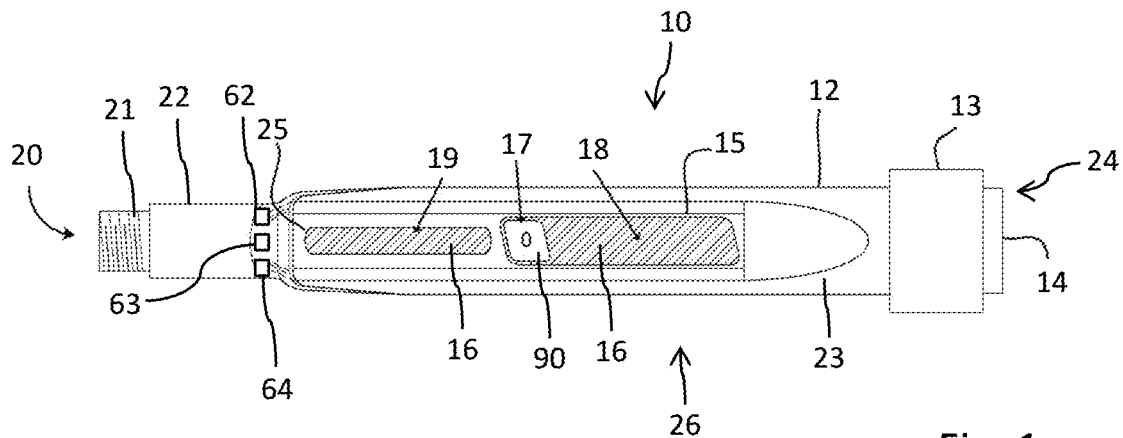
FIG. 1 is a schematic side view of one embodiment of an injection device with a detached protective cap.
Figure 2:
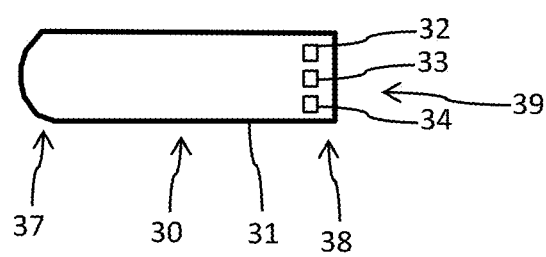
FIG. 2 is another configuration of the device according to FIG. 1.
Figure 2:
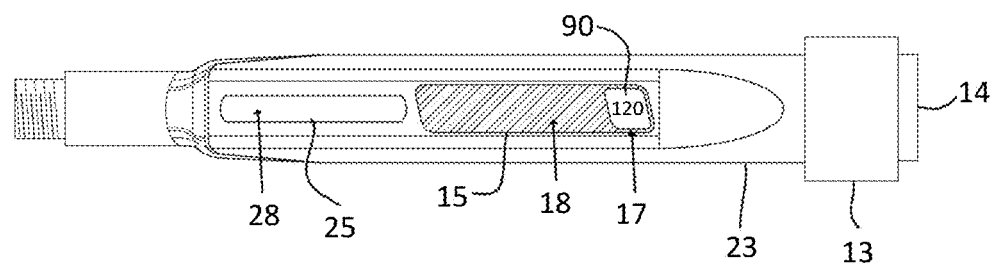
Figure 3:
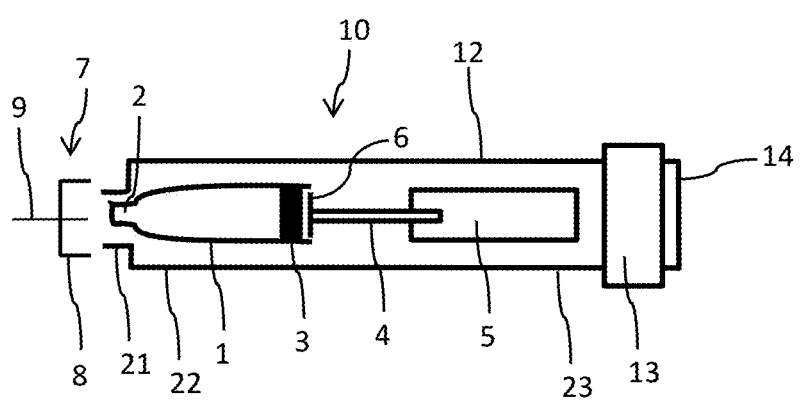
FIG. 3 is a schematic illustration of components of the injection device and their interaction.
Figure 5:
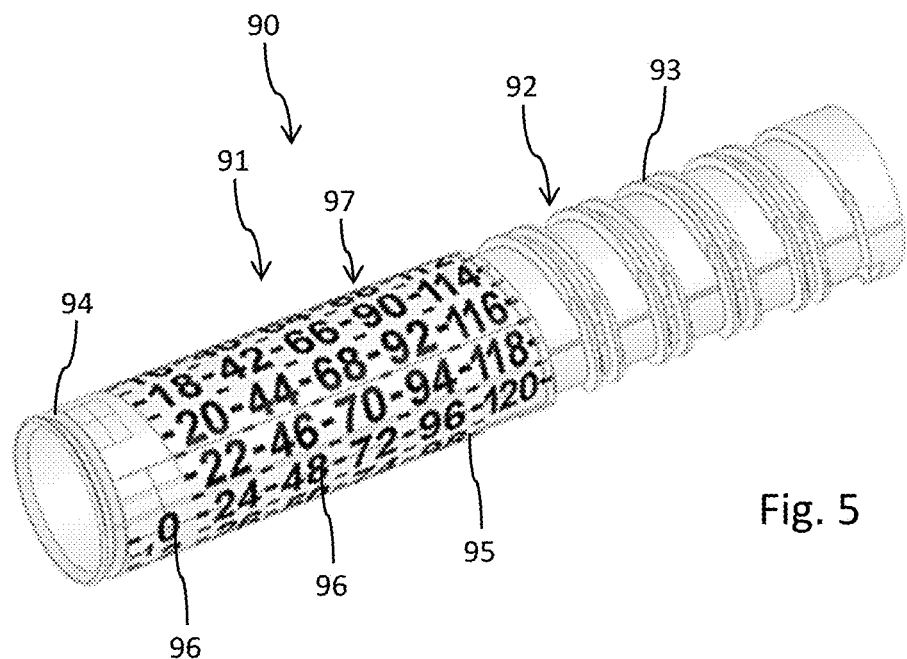
FIG. 5 is a perspective view of one embodiment of a number sleeve and FIG. 6 is a schematic sketch of the number sleeve assembled inside the housing and in electric contact with numerous contact electrodes.

The injection device 10 as exemplary illustrated in FIGS. 1-3 comprises a housing 12 of elongated shape. The elongation of the housing 12 defines an axial direction. The housing 12 may be of substantially cylindrical or oval shape. The housing 12 comprises a distal or a dispensing end 20 at one longitudinal end. At the opposite longitudinal end, namely at the proximal end 24 the injection device 10 comprises a dose selector 13 as well as a dose button 14. The dose selector 13 is of annular shape and is configured to be dialed either clockwise or counter-clockwise to set a dose of a medicament of variable size. The size of a dose actually set is displayed in a gauge window 17. The presently illustrated dose indicating mechanism 26 comprises a number sleeve 90 as illustrated in more detail in FIG. 5.

As the number sleeve 90 is of tubular shape, it comprises a first axial portion 91 and a second axial portion 92. In the first axial portion 91 there is provided a pattern 97 of consecutive dose size indicating numbers 96. The pattern 97 is of helical shape. The helical pattern 97 includes numbers from 0 to 120 in five convolutions. The outside surface 95 of the first portion 91 of the number sleeve 90 is plain and cylindrically-shaped. It is suitable to be printed with the helical pattern 97 of numbers 96. Near a distal end there is provided an annular rim or groove 94 by way of which the number sleeve 90 is axially fixed to the housing 12. Hence, the number sleeve is only free to rotate along its central cylinder long axis but the number sleeve 90 cannot move in axial direction inside the housing 12.

A gauge element 16 as shown in FIGS. 1 and 2 and including the gauge window 17 covers at least a portion of the first portion 91 of the number sleeve 90 that would be otherwise visible through a first window 15 of the housing 12. The size of the gauge window 17 matches with the size of the numbers 96. The gauge element 16 is threadedly engaged with the thread 93 of the number sleeve 90. Moreover, the gauge element 16 is in splined engagement with the housing 12. By means of at least one pair of a radially extending recess mating with a correspondingly-shaped groove the gauge element 16 is rotationally blocked or rotationally fixed to the housing 12. It may only slide along the longitudinal extension of the housing 12 as the number sleeve 90 is subject to a rotation.

Typically, the lead of the thread 93 is identical to the lead of the helical pattern 97. In this way and when the number sleeve 90 is subject to a dose decrementing or dose incrementing rotation the gauge element 16 is subject to a purely axial sliding motion. Due to the combined rotation of the number sleeve 90 and the sliding motion of the gauge element 16 consecutive increasing or decreasing numbers 96 of the helical pattern 97 show up in the gauge window 17. Since the gauge window 17 is located inside the inner circumference of the first window 15 of the housing 12 and since the gauge element 16 is hindered to rotate relative to the housing 12 the gauge window 17 always remains inside the inner circumference of the first window 15.

The housing 12 further comprises a second window 25 that is axially offset to the first window 15. In a zero dose configuration as illustrated in FIG. 1, where no dose is actually set a second portion 19 of the gauge element 16 is located underneath the second window 25. A first portion 18 of the gauge element 16 is located below the first window 15 of the housing 12. As can be seen from FIG. 1, the gauge window 17 of the gauge element 16 is located near a distal end or distal edge of the first window 15 when the injection device 10 or its drive mechanism 5 is in the zero dose configuration. Dialing or setting of a dose by rotating the dose selector 13 is accompanied by a rotation of the number sleeve 90 and with an axial sliding displacement of the gauge element 16 towards the proximal end 24.

During a dose increasing dialing the gauge element 16 in its entirety moves from the distal zero dose configuration as shown in FIG. 1 towards a maximum dose configuration as shown in FIG. 2. Consequently, the second portion 19 of the gauge element 16 moves into the first window 15 so that the gauge element 16 is no longer apparent in the second window 25 when a maximum dose configuration has been reached as illustrated in FIG. 2. Typically, as the distal end of the gauge element 16 moves out of the second window 25 in proximal direction a background 28 becomes apparent in the second window 25. The visual appearance, e.g. the color or texture of the background 28 and of the gauge element 16 drastically or clearly differ from each other. In effect, that portion of the gauge element 16 that shows up in the second window 25 in comparison to the total axial elongation of the window 25 is directly indicative of a size of a dose actually set.

It is to be noted here, that the present dose indicating mechanism 26 is only exemplary and that some aspects can be generally implementable with any kind of dose indicating mechanism currently known for hand held pen-type injection devices. It is generally conceivable, that the number sleeve 90 is subject to a helical screw motion during dose setting as well as during dose dispensing.

The housing 12 may be a single piece or may comprise multiple components. Near the distal or dispensing end 20 the housing 12 comprises a cartridge holder portion 22. This section of the housing 12 is configured to accommodate and to hold a cartridge 1 as schematically illustrated in FIG. 3. The distal end or the dispensing end 20 is further provided with a threaded socket 21 to receive and to engage with a needle assembly 7 having a cup-shaped needle hub 8 and a double-tipped injection needle 9. When screwed or otherwise attached to the dispensing end the injection needle 9 penetrates a distal seal 2 of the cartridge 1 located inside the housing 12. A proximal end of the tubular barrel of the cartridge 1 is typically sealed by a rubber piston 3.

As it is illustrated in FIG. 3, the body portion 23 of the housing 12 accommodates a drive mechanism 5 which is only schematically illustrated in FIG. 3. The drive mechanism 5 comprises numerous mechanically engaging components, inter alia at least a piston rod 4 with a pressure piece 6 at its distal end. The drive mechanism 5 is operable to displace the piston rod 4 in distal direction, hence towards the cartridge 1 in order to displace the piston 3 of the cartridge in distal direction so as to expel a well-defined amount of the medicament through the injection needle 9. Further details of a drive mechanism 5 or of a dose indicating mechanism 26 are generally known in the art, in particular from document WO 2014/166926 A1, the entirety of which is herein incorporated by reference.

When not in use the needle assembly 7 should be detached from the injection device 10. In order to protect the dispensing end 20 the injection device 10 is further equipped with a protective cap 30, which is schematically illustrated in FIG. 1. The protective cap 30 comprises a tubular-shaped cap body 31 with a closed end 37 at its distal end and with an oppositely located proximal end 38 having an insert opening 39 to receive at least the cartridge holder portion 22 of the housing 12 of the injection device 10. The cap body 31 may be of substantially cylindrical shape. The cap body 31 and the housing 12 comprise mutually corresponding and inter-engageable fastening elements (not illustrated) by way of which the protective cap 30 can be fastened and kept in a well-defined orientation and position to the housing 12. The cap 30 and the housing 20 may comprise at least one symmetry breaking feature (not shown) so that the cap 30 can be attached and fastened to the housing in only one pre-defined orientation.

The cap 30 is provided with at least one cap electrode 32, 33, 34 and the housing 12 is provided with at least one housing electrode 62, 63, 64. The cap electrodes 32, 33, 34 may be provided on an inside of a sidewall portion of the cap body 31 whereas the housing electrodes 62, 63, 64 are provided on the outer surface of the housing 12. When the cap 30 is assembled to the housing 12 in a predefined assembly configuration each one of the cap electrodes 32, 33, 34 is in contact with one of the housing electrodes 62, 63, 64. By means of the cap electrodes 32, 33, 34 and the housing electrodes 62, 63, 64 an electric contact between the cap 30 and the housing 12 can be established.

Figure 4:
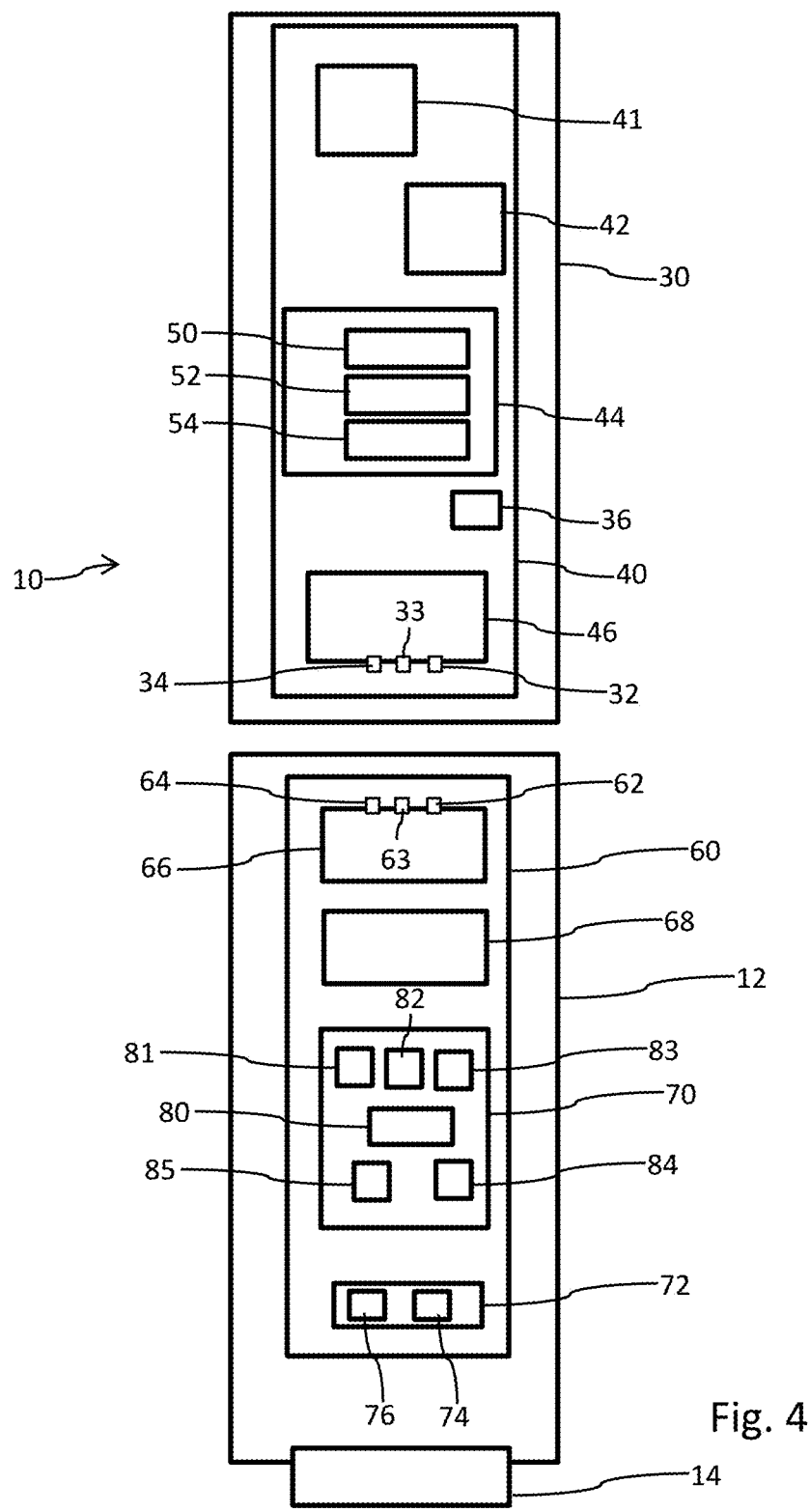
FIG. 4 is a block diagram of the protective cap and the housing with first and second electronic circuits.

The cap 30 is further provided with a first electronic circuit 40 as illustrated in FIG. 4. In the present embodiment the first electronic circuit 40 is provided with a first logic circuit 44, with an energy supply 41, typically in form of a battery and with a transceiver 42. Furthermore, the first electronic circuit 40 comprises an interface 46 electrically connected to the logic circuit 44. The interface 46 is provided with at least one cap electrode 32, 33, 34.

In typical embodiments the first logic circuit 44 is provided with a real time clock 50, a memory 52 and a processor 54, such as a micro-controller or the like. The entire electronic circuit 40 may be implemented on a printed circuit board. At least the logic circuit 44 is provided on a printed circuit board. The transceiver 42 may provide a wireless or wired communication with further analysis tools, such like personal computers, tablet computers or smartphones. The transceiver 42 may be configured as a Bluetooth transceiver, e.g. as a Bluetooth Low Energy (BLE) transceiver. Alternatively or additionally the transceiver may operate according to other short-range wireless communication standards, such like IEEE802.11, also denoted as wireless LAN or Wi-Fi. Additionally or alternatively the transceiver 42 may comprise a loudspeaker for acoustic transmission of information and data. It is also conceivable, that the transceiver 42 is an infrared transceiver operating in accordance to the so-called IrDA-standard. When implemented as a wired transceiver 42 it may comprise a socket or plug, such like a Universal Serial Bus (USB) interface.

The first electronic circuit 40 is configured as a main electronic circuit of the injection device 10 that is capable to capture, to collect and to process electric signals transmitted by and received from a second electronic circuit 60 that is implemented and located inside the housing 12 of the injection device 10. The second electronic circuit 60 is configured and implemented as an auxiliary electronic circuit that is cut down compared to the first electronic circuit 40. The second electronic circuit 60 may be void of an own energy supply. It may be void of a battery. The second electronic circuit 60 is also void of a transceiver. The second electronic circuit 60 may even be void of a logic circuit. The second electronic circuit 60 may be as simple as to provide a couple of wires and contact electrodes 101, 102, 103 as for instance illustrated in FIG. 6. Each one of the contact electrodes 101, 102, 103 may be separately connected to one of the housing electrodes 62, 63, 64.

In the embodiment presently illustrated in FIG. 4, the second electronic circuit 60 comprises an interface 66 with three housing electrodes 62, 63, 64. The second electronic circuit 60 further comprises a battery 68. The battery 68 is typically of rechargeable type. It is of particular benefit, when the capacity of this second battery 68 is much smaller than the capacity of the first battery 41. Since the first battery 41 is in electrical contact with the interface 46 and hence with the cap electrodes 32, 33, 34 and since the second battery 68 is in electrical contact with the interface 66 and hence with the housing electrodes 62, 63, 64 the second battery 68 implemented as a cut-down or auxiliary battery can be re-charged by means of the first battery 41.

The second electronic circuit 60 further comprises a second logic circuit 70. The functionality, the size as well as manufacturing costs of the second logic circuit 70 are less than those of the first logic circuit 44. Optionally the second electronic circuit 40 comprises a sensor assembly 72. The sensor assembly 72 may comprise at least one of a resistor assembly 74 and contact switches 76.

The second logic circuit 70 may comprise a second processor 80 as well as a memory 81, a wire interface 82 and a counter 83. Furthermore, the second logic circuit 70 may comprise an Analogue Digital Converter (ADC) 84 as well as a reference voltage supply 85 for the ADC to operate.

When the cap 30 is correctly assembled to the housing 12 the cap electrodes 32, 33, 34 and the housing electrodes 62, 63, 64 are in mutual electrical contact. In this way also the first electronic circuit 40 and the second electronic circuit 60 are in electrical contact. In the present embodiment with three cap electrodes 32, 33, 34 and with three correspondingly configured housing electrodes 62, 63, 64 two pairs of electrodes, e.g. electrodes 34, 64 and electrodes 32, 62 may provide a kind of a power supply for the second battery 68 and/or for the second logic circuit 70. A third pair of electrodes, namely the housing electrode 63 in contact with the cap electrode 33 may provide data or signal transmission between the first and second electronic circuits 40, 60 and/or between first and second logic circuits 44, 70.

For instance electric signals measured or pre-processed by the second logic circuit 70 can be transmitted via the interfaces 66, 46 to the first logic circuit 44. There, the obtained signals or pre-processed data can be further processed and can be provided to the transceiver 42 for further transmission to other, external electronic devices.

It is also conceivable, that a clock signal provided by a real time clock 50 is transmitted via the interfaces 46, 66 to the second logic circuit 70. Since the second logic circuit 70 also comprises an own memory 81, e.g. implemented as a non-volatile memory, such as a flash memory, signals that are pre-processed or processed by the second processor 80 can be at least temporally stored in the memory 81. By means of the clock signal obtained from the first electronic circuit 60 the second logic circuit 70 may assign a timestamp to the data that is locally stored in the memory 81.

The second logic circuit 70 may be directly connected to the sensor assembly 72. In a rather simple embodiment the sensor assembly 72 comprises numerous, i.e. at least two contact switches that are engaged with at least one or several components of the drive mechanism 5. Depending on the specific implementation of the drive mechanism 5 the contact switches 76 will be closed or open depending on the actual state and configuration of the drive mechanism 5.

By means of contact switches counting pulses generated during a dose setting or dose dispensing can be electrically tracked and counted in order to calculate a size of a dose actually set or actually dispensed and injected.

Figure 6:
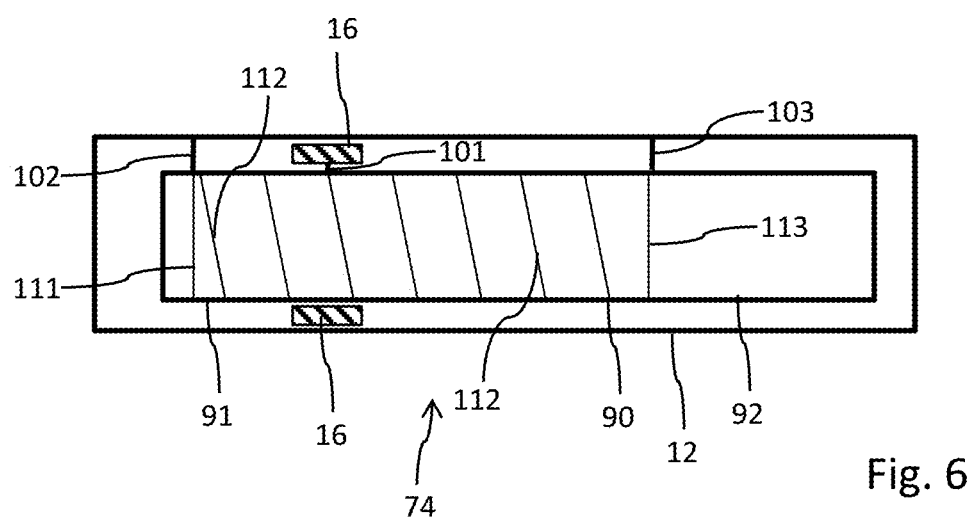

The sensor assembly 72 may be configured as a resistor assembly 74, which is schematically illustrated in more detail in FIG. 6. The resistor assembly 74 comprises at least one electric resistor strip 112 extending on the outside surface 95 of the number sleeve 90. In the present embodiment and with the presently described dose indicating mechanism 26 the electric resistor strip 112 extends on the outside surface of the number sleeve 90 in accordance with the helical pattern 97 of the dose size indicating numbers 96. The electric resistor strip 112 may overlap with the number pattern 97. It is generally conceivable, that the electric resistor strip 112 extends axially between consecutive convolutions of the helical pattern 97 of the dose size indicating numbers 96.

The electric resistor strip 112 may be printed in a rather cost-efficient manner on the outside surface 95 of the number sleeve 90. The electric resistor strip 112 does not necessarily have to overlap with the helical pattern 97 of the dose size indicating numbers 96. It may be separated axially therefrom.

The electric resistor strip 112 exhibits a linear or proportional behavior of its electrical resistivity over total length. An increase in electrical resistivity of the electric resistor strip is directly proportional to an increase of the total length of the electric resistor strip 112. As illustrated in FIG. 6, the gauge element 16 surrounding at least a portion of the number sleeve 90 comprises a first contact electrode 101 pointing radially inwardly to get in contact with the electric resistor strip 112. As the number sleeve 90 is subject to a dose increasing or dose decreasing rotation the gauge element 16 actually moves along the number sleeve 90. Since the lead of the helically-shaped resistor strip 112 is identical or substantially identical to the lead of the threaded engagement between the number sleeve 90 and the gauge element 16 the first contact electrode 101 remains in a permanent electrical contact with the electric resistor strip 112.

In axial direction the helical resistor strip 112 is sandwiched between a first annular tab 112 and a second annular tab 113. The annular tabs 111, 113 encircle the entire outer circumference of the number sleeve 90. They are further in electrical contact with opposite ends of the helically-shaped electric resistor strip 112.

There are provided two further contact electrodes, namely a second contact electrode 102 in contact with the first annular tab 111 and a third contact electrode 103 in permanent electrical contact with the second annular tab 113. Second and third contact electrodes 102, 103 are permanently fixed to the housing 12. The contact electrodes 102, 103 point radially inwardly to stay in contact with the first and with the second annular tabs 111, 113, respectively.

The contact electrodes 101, 102, 103 are in electrical contact with the second logic circuit 70. The second logic circuit 70, alternatively the first logic circuit 44 is configured and operable to calculate a ratio of a first electrical resistivity R1 and a total electrical resistivity R2 of the helical resistor strip 112. At least one of the first and the second logic circuits 44, 70 is able to calculate this particular ratio. Here, the first electrical resistivity R1 is measurable for instance between the first contact electrode 101 and the second contact electrode 102. The total electrical resistivity is measurable between the second contact electrode 102 and the third contact electrode 103, hence between first and second annular tabs 111, 113.

By dividing the first electrical resistivity R1 by the total electrical resistivity R2 the resistivity measurement is rather insensitive to temperature deviations. A temperature-induced change of the electrical resistivity equally applies to both, the first electrical resistivity and the total electrical resistivity. By dividing the first electrical resistivity by the total electrical resistivity a temperature-induced drift or offset of a resistivity measurement can be leveled out.

The above described injection device 10 is mainly configured as a disposable device, i.e. the housing 12 and all components located therein are intended to be discarded after use or after consumption of the content of the cartridge 1. The protective cap 30 is configured and designed as a reusable device that can be coupled and engaged with a sequence of disposable housings.

There exist several user scenarios. For instance, a disposable housing 12 with a rather cut-down electronic circuit 60 may comprise an auxiliary battery as the second battery 68 that is charged by the first battery 41 of the protective cap 30 as long as the protective cap 30 is attached to the housing 12. If the protective cap 30 is detached from the housing 30 the second electronic circuit 60, in particular the second logic circuit 70 will be operable for a limited period of time, such like 30 minutes or one hour. During this time interval the cut-down second logic circuit 70 may autonomously record or capture dose setting or dose dispensing-related electric signals or respective data. Prior to the disconnection of the protective cap 30 from the housing 12 a timestamp is provided by the real time clock 50 to the second logic circuit 70. In this way the logic circuit 70 is operable to store a time information together with a dose information in a local memory 81 without the necessity of implementing an own real time clock in the second logic circuit 70 or the second electronic circuit 60.

When the protective cap 30 is re-assembled to the housing 12 data stored previously in the local memory 81 may be transmitted via the interfaces 66, 46 to the first logic circuit 44. There, the data may be processed further and stored in a larger memory 52. On demand or at regular time intervals the data stored in the memory 52 can be transferred to an external electronic device via the transceiver 42.

It is to be noted, that a measurement of the revolutions of the number sleeve 90 on the basis of a resistivity measurement is only exemplary. Likewise a revolution or degree of rotation of the number sleeve 90 could be equally detected with the help of capacitive sensors or magnetic sensors. Moreover, and as illustrated in FIG. 4, a microphone 36 may be provided to the first electronic circuit 40. By means of a microphone 36, audible clicking noises generated by the drive mechanism 5 during dose setting and/or dose dispensing can be recorded and counted. By counting a number of subsequent clicking sounds or similar noise allows calculating a respective size of a dose, in particular when each clicking sound represents a well-defined interval of standard units of the medicament.

LIST OF REFERENCE NUMBERS 1 cartridge
2 seal
3 piston
4 piston rod
5 drive mechanism
6 pressure piece
7 needle assembly
8 needle hub
9 injection needle
10 injection device
12 housing
13 dose selector
14 dose button
15 first window
16 gauge element
17 gauge window
18 first portion
19 second portion
20 dispensing end
21 threaded socket
22 cartridge holder portion
23 body portion
24 proximal end
25 second window
26 dose indicating mechanism
28 background
30 protective cap
31 cap body
32 cap electrode
33 cap electrode
34 cap electrode
36 microphone
37 closed end
38 open end
39 opening
40 electronic circuit
41 battery
42 transceiver
44 logic circuit
46 interface
50 real time clock
52 memory
54 processor
60 electronic circuit
62 contact electrode
63 contact electrode
64 contact electrode
66 interface
68 battery
70 logic circuit
72 sensor assembly
74 resistor assembly
76 contact switch
80 processor
81 memory
82 interface
83 counter
84 analogue digital converter
85 reference voltage supply
90 number sleeve
91 first portion
92 second portion
93 thread
94 groove
95 outside surface
96 number
97 pattern
101 contact electrode
102 contact electrode
103 contact electrode
111 annular tab
112 resistor strip
113 annular tab

The invention claimed is:
1. An injection device for administering a dose of a liquid medicament, the injection device comprising:

an elongated housing having a dispensing end and being configured to accommodate a cartridge containing the liquid medicament;

a drive mechanism configured to operably engage with the cartridge for expelling the dose of the liquid medicament from the cartridge via the dispensing end of the housing;

a protective cap releasably attachable to the housing to cover the dispensing end of the housing;

a first electronic circuit attached to the protective cap and electrically connected to a cap electrode arranged on the protective cap, wherein the first electronic circuit comprises a transceiver operable to transmit data to an external analysis device; and a second electronic circuit attached to the housing, coupled to the drive mechanism and electrically connected to a housing electrode that is located on the housing, wherein the first and the second electronic circuits are electrically connectable to each other via the cap electrode and the housing electrode, the cap electrode and the housing electrode being configured to get in mutual contact when the protective cap is attached to the housing, and wherein the second electronic circuit is void of a transceiver.

2. The injection device according to claim 1, wherein the first electronic circuit comprises a first battery and a first logic circuit to process electric signals received from the second electronic circuit.

3. The injection device according to claim 2, wherein the second electronic circuit comprises a second logic circuit to capture dose dispensing related data from the drive mechanism and to transmit the captured dose dispensing related data to the first logic circuit via the cap electrode and the housing electrode.

4. The injection device according to claim 3, wherein the second logic circuit is powered by the first battery when the protective cap is attached to the housing.

5. The injection device according to claim 4, wherein the second electronic circuit comprises a re-chargeable second battery that is chargeable by the first battery when the protective cap is attached to the housing.

6. The injection device according to claim 1, wherein the transceiver is a wireless transceiver.

7. The injection device according to claim 1, wherein only the first electronic circuit is provided with the transceiver.

8. The injection device according to claim 1, wherein the second electronic circuit is void of a battery.

9. The injection device according to claim 1, wherein the second electronic circuit is void of a logic circuit.

10. The injection device according to claim 1, wherein the drive mechanism comprises at least one of:
a dose selector to set a dose of the liquid medicament of a variable size, wherein the dose selector is audibly movable relative to the housing at predefined discrete steps, or
a dose button audibly movable relative to the housing to trigger or to control a medicament dispensing procedure.

11. The injection device according to claim 10, wherein the first electronic circuit comprises a microphone to detect successive dose incrementing steps or dose decrementing steps of a movement of the dose selector and/or to detect a movement of the dose button.

12. The injection device according to claim 10, wherein the second electronic circuit comprises a contact switch connected to the housing electrode and connected to the drive mechanism.

13. The injection device according to claim 1, wherein the drive mechanism comprises a number sleeve rotatably supported inside the housing, the number sleeve comprising:
a pattern of dose size indicating numbers on an outside surface, and
an electric resistor strip extending on the outside surface in accordance with the pattern.

14. The injection device according to claim 13, wherein the second electronic circuit comprises a first contact electrode in contact with the electric resistor strip.

15. The injection device according to claim 1, further comprising a cartridge arranged inside the housing and being filled with the liquid medicament.

16. A protective cap for a dispensing end of an injection device, the protective cap comprising:
a cap body;
a cap electrode attached to the cap body; and
a first electronic circuit attached to the cap body and electrically connected to the cap electrode, the first electronic circuit comprising a transceiver operable to transmit data to an external analysis device,
wherein the first electronic circuit is configured to be electrically connected to a second electronic circuit of the injection device via the cap electrode when the protective cap is attached to the injection device, wherein the second electronic circuit is configured to capture dose dispensing related data from a drive mechanism of the injection device.

17. The protective cap according to claim 16, wherein the first electronic circuit comprises a first battery and a first logic circuit, wherein the first logic circuit is operable to receive electric signals from the second electronic circuit of the injection device via the cap electrode, wherein the electric signals are indicative of the dose dispensing related data and wherein the first logic circuit is operable to transmit the dose dispensing related data to the external analysis device via the transceiver.

18. A kit configured to provide an injection device for administering a dose of a liquid medicament, the kit comprising:
a disposable elongated housing having a dispensing end and being configured to accommodate a cartridge filled with the liquid medicament;
a drive mechanism arranged inside the elongated housing and configured to operably engage with the cartridge for expelling of the dose of the liquid medicament from the cartridge via the dispensing end;
a reusable protective cap detachably attached to the housing to cover the dispensing end;
a first electronic circuit attached to the protective cap and electrically connected to a cap electrode arranged on the protective cap, wherein the first electronic circuit comprises a transceiver operable to transmit data to an external analysis device; and
a second electronic circuit arranged inside the housing, coupled to the drive mechanism and electrically connected to a housing electrode located on the housing,
wherein the first and the second electronic circuits are electrically connectable to each other via the cap electrode and the housing electrode, the cap electrode and the housing electrode being configured to get in mutual contact when the protective cap is attached to the housing, and wherein the second electronic circuit is void of a transceiver.

19. A method of monitoring a medicament dispensing operation, the method comprising:
   initiating the medicament dispensing operation with an injection device such that an electronic circuit of the injection device captures dose dispensing related data for the medicament dispensing operation; and
   attaching a protective cap to the injection device, thereby causing an electronic circuit of the protective cap to receive the dose dispensing related data from the electronic circuit of the injection device and to transmit the dose dispensing related data to an external analysis device exclusively via a transceiver of the electronic circuit of the protective cap.

* * * * *